(12) United States Patent
Farley et al.

(10) Patent No.: US 8,705,038 B2
(45) Date of Patent: Apr. 22, 2014

(54) DUCT DETECTOR

(75) Inventors: Daniel G. Farley, Westminster, MA (US); Anthony J. Capowski, Westford, MA (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 248 days.

(21) Appl. No.: 12/946,708

(22) Filed: Nov. 15, 2010

(65) Prior Publication Data

US 2012/0120399 A1     May 17, 2012

(51) Int. Cl.
*G01N 21/00*     (2006.01)
(52) U.S. Cl.
USPC .......................... 356/438; 250/574; 356/338
(58) Field of Classification Search
USPC ................. 356/432–440, 244, 246, 335–343; 250/349, 343, 574–576
See application file for complete search history.

(56) References Cited

U.S. PATENT DOCUMENTS

| | | | | |
|---|---|---|---|---|
| 3,600,590 A * | 8/1971 | Einstein | ........................ | 250/574 |
| 3,796,887 A * | 3/1974 | Vincent et al. | ................ | 250/565 |
| 4,069,711 A * | 1/1978 | Muschelknautz et al. | ... | 73/61.66 |
| 4,560,873 A * | 12/1985 | McGowan et al. | ...... | 250/339.09 |
| 4,651,004 A * | 3/1987 | Uno et al. | ..................... | 250/343 |
| 5,089,000 A * | 2/1992 | Agee et al. | ..................... | 606/170 |
| 5,170,064 A * | 12/1992 | Howe | ........................... | 250/573 |
| 5,636,918 A * | 6/1997 | Lott | .............................. | 362/139 |
| 6,193,386 B1 * | 2/2001 | Reynolds | ...................... | 362/109 |
| 6,943,885 B2 * | 9/2005 | Martin | .......................... | 356/437 |
| 7,909,520 B2 * | 3/2011 | Barab | ........................... | 396/420 |
| 2005/0119670 A1 * | 6/2005 | Kerr | .............................. | 606/144 |

* cited by examiner

*Primary Examiner* — Hoa Pham
(74) *Attorney, Agent, or Firm* — Kacvinsky Daisak PLLC (57) ABSTRACT

A particle detection unit including a detection chamber and a duct detector is disclosed. The duct detector is disposed within the detection chamber. The duct detector has a rod with a first and a second end where the first end is distal the second end. A reflector may be attached to the rod adjacent the first end. A sensor and emitter device may be attached to the rod and spaced apart from the reflector.

14 Claims, 5 Drawing Sheets

DUCT DETECTOR

BACKGROUND OF THE INVENTION

1. Field of the Invention

Embodiments of the present disclosure relate to the field of duct or chamber systems. More particularly, the present disclosure relates to a system and method for detecting unwanted foreign particles within a duct or air handling system.

2. Discussion of Related Art

In air handling or ventilation systems (HVAC), fans draw fresh outside air into a building, and exhaust stale interior air to the outside. These air handling systems use venting or ducts (i.e. ductwork) to provide an air flow path throughout the building, including to and from heaters and/or air conditioners. To assist in adjusting the volume of air flow, volume control dampers and fans may be used. These dampers and fans can be fitted within the ducts themselves and may be manually or automatically activated.

On occasion, unwanted foreign particles may enter the ductwork of such air handling systems. For example, in the case of a fire, smoke may enter the ductwork. To control the spread of smoke throughout the duct system and subsequently other rooms of the building, smoke dampers may be used which may be automated with the use of a mechanical motor, often referred to as an actuator. For example once smoke is detected by a sensor within the duct, the sensor sends a signal to the actuator to close the smoke damper. A signal may also be sent from the sensor to shut down the fans thereby limiting the spread of smoke through the ducts which would otherwise travel to other rooms or parts of the building. Thus, detectors/sensors may be located throughout the ductwork of a building to detect the presence of smoke which triggers the control of fans and dampers to prevent smoke from traveling or spreading to unwanted areas therein.

Figure 1:
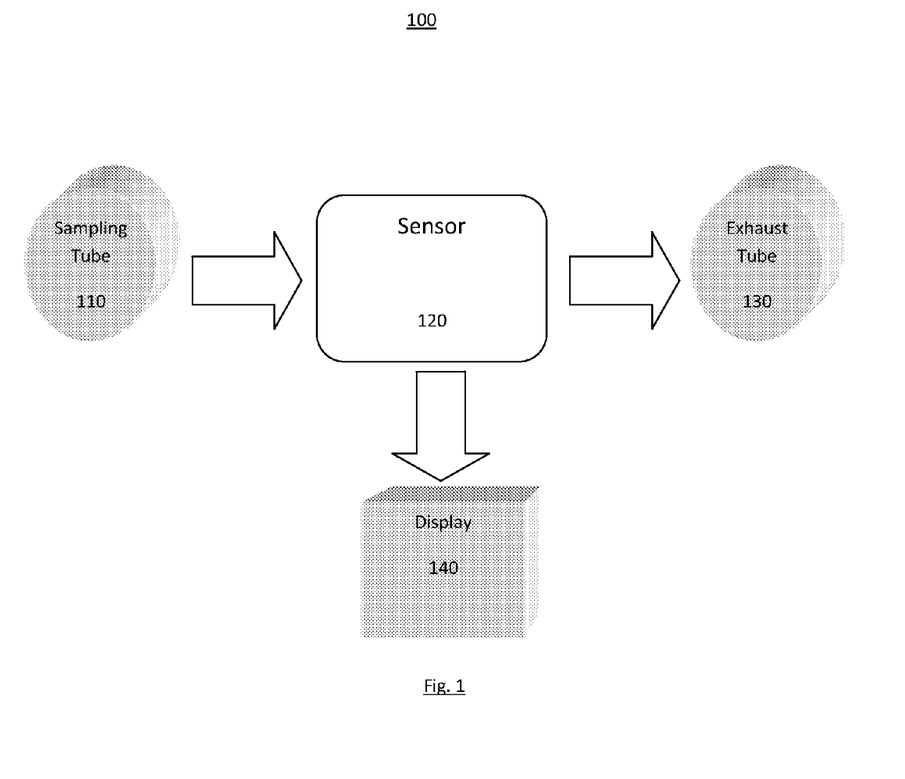
FIG. 1 is a functional diagram of a conventional duct sensor.

FIG. 1 is a functional depiction of a conventional duct sensor 100 used to detect smoke within a duct. The duct sensor 100 includes a sampling tube 110, a smoke sensor 120, and exhaust tube 130. The sampling tube 110 is used to collect the smoke and then to guide the air through the smoke sensor 120. After passing through the smoke sensor 120, the air is then released through the exhaust tube 130. If smoke is detected by the smoke sensor 120, display 140 indicates the detection of smoke by the duct sensor 100. Those of ordinary skill in the art will recognize that the depicted system is highly-simplified for ease of explanation.

Figure 2:
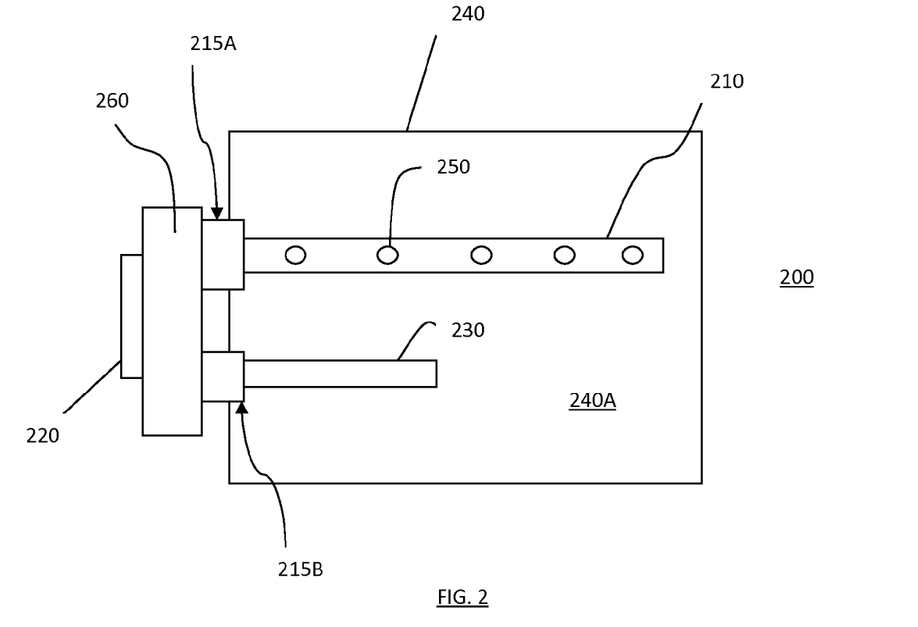
FIG. 2 is a cross sectional view of a conventional duct sensor attached to a duct.

FIG. 2 illustrates a cross-sectional view of conventional duct sensor 200 attached to duct 240, the walls of which define duct chamber 240a. Smoke sensor 220 is attached to housing 260 and is located outside of duct 240. Housing 260 is connected to exhaust tube 230 and sampling tube 210. To attach housing 260 to duct 240, two holes 215A and 215B must be formed in a wall of the duct to allow sampling tube 210 and exhaust tube 230 to project into duct chamber 240a respectively. As such, this requires two holes for every duct sensor that is attached to a portion of the ductwork. To prevent room particles from entering the duct system or duct particles from entering the room, gaskets or other means (not shown) must be used to seal the two holes. Thus, there exists a need for a new and improved duct sensor/detector to reduce the number of holes that need to be created in a duct system.

Sampling tube 210 also includes access holes 250 for capturing air that flows through duct 240. To prevent sampling tube 210 from recapturing exhausted smoke from exhaust tube 230, sampling tube 210 must be located upstream of exhaust tube 230. This means that exhaust tube 230 must be positioned downstream of sampling tube 210 when attaching the duct sensor 200 to the duct system. Thus, conventional duct sensor 200 must be properly oriented to allow the duct to funnel air in through sampling tube 210, across sensor 220 via housing 260, and out through exhaust tube 230. Hence, there exists a need for a new and improved duct sensor to eliminate possible orientation errors when installing a duct sensor/detector.

Furthermore, air must be flowing through the duct to allow conventional sensor 220 to sample the air in the duct. Therefore, before a conventional duct sensor 200 can be properly tested to make sure the smoke sensor 220 is operating properly, it must be verified that air is flowing within the duct. Thus, in an effort to properly test the smoke sensor 220 and to make sure air is flowing within the duct, a device may be required to be placed within the duct before testing. This device measures the airflow or differential pressure of the duct to indicate whether or not airflow is present around the sensor 220. Without these additional devices, it may be impossible to know whether the smoke supplied for testing has reached the sensor 220 or if the smoke has traversed through the device that measures differential pressure which may compromise testing. Thus, there exists a need for a new and improved duct sensor/detector to eliminate the need for air flow testing.

SUMMARY OF THE INVENTION

Exemplary embodiments of the present disclosure are directed to a particle detection unit including a detection chamber; a duct detector disposed within the detection chamber, comprising a rod having a first and a second end, the first end distal the second end, a reflector attached to the rod adjacent the first end, and a sensor/emitter device attached to the rod and spaced apart from the reflector at the second end wherein particles disposed between the first and second ends are detected.

In another exemplary embodiment, a particle detection unit includes a detection chamber; a duct detector disposed at least partially within the detection chamber, and having a sensor attached to an inner wall of the detection chamber. An emitter is attached to the inner wall of the detection chamber opposite the sensor. In another exemplary embodiment, a particle detection unit includes a detection chamber and a duct detector, disposed within the chamber which is defined by a rod having a first and a second end. The first end is distal the second end. An emitter is attached to the rod adjacent the first end, and a sensor is attached to the rod and spaced apart from the reflector.

In an exemplary method, a duct detector is installed within a detection chamber defined by a wall having an inner surface. The duct detector is attached to the inner surface of the duct and smoke is detected within the chamber. The duct detector comprises a rod having a first and a second end. The first end is distal the second end and a reflector is attached to the rod adjacent the first end. A sensor and emitter device is attached to the rod and spaced apart from the reflector.

DETAILED DESCRIPTION

The present disclosure will now be described more fully hereinafter with reference to the accompanying drawings, in which preferred embodiments of the invention are shown. This invention, however, may be embodied in many different forms and should not be construed as limited to the embodiments set forth herein. Rather, these embodiments are provided so that this disclosure will be thorough and complete, and will fully convey the scope of the invention to those skilled in the art. In the drawings like numbers refer to like elements throughout.

Figure 3:
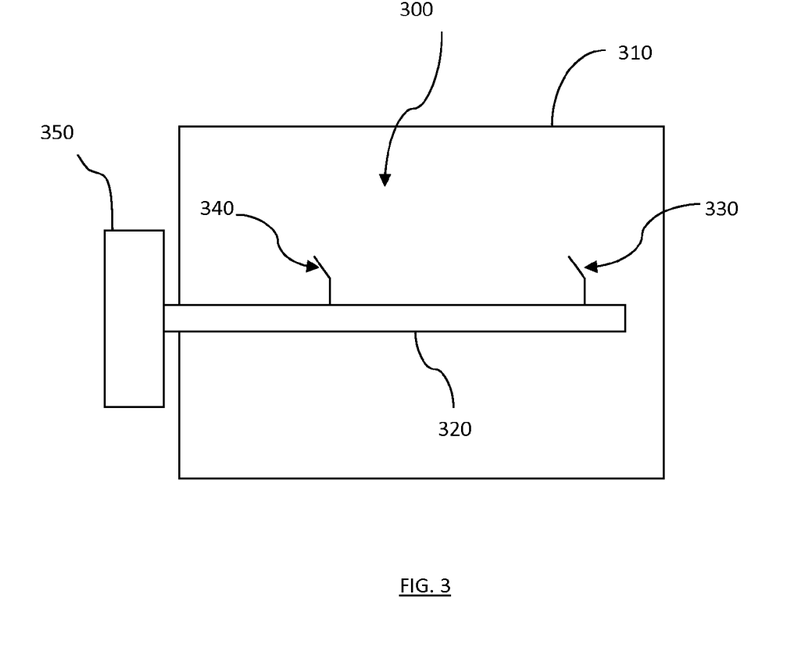
FIG. 3 is a cross sectional view of a duct detector in accordance with the present disclosure.

FIG. 3 shows a cross-sectional view of an exemplary duct detector 300 consistent with one embodiment of the present disclosure. Those of ordinary skill in the art will recognize that the depicted system is highly-simplified for ease of explanation. In this exemplary embodiment, the duct detector 300 is inserted and attached to an air duct 310. The shape of the duct is defined by the duct walls. Generally, an improved duct detector is inserted or attached to any chamber or other confined space such as, for exemplary purposes only, ductwork, plenums, air handlers, silos, etc.

Duct detector 300 includes a rod 320 which has a reflector 330 coupled to the distal end of the rod 320. A sensor and emitter (sensor/emitter) device 340 is spaced apart from the reflector 320 and is also coupled to the rod 320. The sensor and emitter device 340 may contain both a light sensor and emitter. As depicted, the rod 320 including the reflector 330, and sensor and emitter device 340, is inserted into the chamber of duct 310. To insert duct detector 300 into the duct 310, a single penetration hole (not shown to scale) may be made in the duct 310 the size of which is dependent on the size of the sensor and emitter device 340, rod 320, and reflector 330. The rod may be hollow to accommodate wiring to and from the sensor and emitter device 340 and reflector 330. The rod 320 may then be attached, for example, to the duct 310 by any means known in the art. Thus, with this embodiment only a single penetration hole may be created in the duct 310 housing to accommodate rod 320, reflector 330, and sensor and emitter device 340. This embodiment advantageously reduces the number of holes needed in the duct housing as compared to using a conventional duct detector 200 where two holes must be created to allow for sampling tube 210 and exhaust tube 230 to penetrate into the duct as shown in FIG. 2.

With this embodiment, the sensor/emitter device 340 and the reflector 330 are used to detect particles (i.e., smoke) within the duct. The reflector 330 along with the sensor/emitter device 340 use technology that is similar to a beam detector for detecting particles (i.e., smoke) in the air. In particular, light from the emitter portion of emitter/sensor 340 is transmitted within the duct 310 toward reflector 330 which reflects the light back toward sensor portion of emitter/sensor 340. When particles are present within the air within duct 310, the sensor portion of emitter/sensor 340 will not receive the same amount of light emitted by the emitter portion of emitter/sensor 340. More specifically, it is the difference between the amount of light produced by the emitter and the amount of light received by the sensor via the reflector 330, as well as the distance between the sensor 340 and reflector 330 which is used to calculate the percentage of obstructed light. This percentage of light obstruction is used to determine the presence of unwanted particles (i.e., smoke) between the emitter and the sensor. Generally, percent obscuration is reported per foot. Thus, if the distance between the emitter and sensor is, for example, 12 inches then the percent obscuration is the real value. However, if the distance between the emitter and sensor is 6 inches, then the percent obscuration is reported as two times the value since the light is only going half the distance. Thus, when the percentage of obstructed light exceeds a predetermined threshold an alarm is triggered. The duct detector 300 communicates with alarm indicating devices via control modules and/or control panels through wired or wireless connections 350 which may be, for example, bells, alarms, LED indicators, displays, etc.

By inserting the sensor and emitter device 340 into the duct 310, the duct detector 300 uses the duct itself as a chamber for detecting particles (i.e., smoke). Thus, rather than placing the sensor and emitter device 340 outside of the duct and guiding the air across the sensor as in duct sensor 200 described above, the sensor and emitter device 340 are placed within the duct 310, thereby eliminating the need to test whether or not air is flowing prior to testing the sensors. In this manner, the need to use airflow and differential pressure devices to detect airflow within the duct 310 prior to the testing is advantageously eliminated.

Likewise, because the duct 310 may now be used as the sensing chamber, the duct detector 300 eliminates the orientation problems described above with respect to conventional smoke detector 200. More specifically, upstream and downstream orientation concerns regarding sampling tube 210 and exhaust tube 230 are eliminated. The airflow is no longer depended on to guide the smoke out of the duct to the sensor 220. The sensor and emitter device 340 are now located within the duct itself. In addition, the spacing between the sensor/emitter and thus the distance the light travels from the sensor portion of emitter/sensor 340 to reflector 330 and back to the sensor portion of emitter/sensor 340 may be much closer as compared to convention beam detectors.

Groups of duct detectors may be installed within an air handling systems and wired together along a pair of bidirectional communication lines. A group of such devices on a pair of lines is often referred to as a "line of devices." Many lines of devices can connect back to a control panel that controls the operation of an alarm system. A line of devices is usually associated with a certain zone of the building and/or a certain type of device. For example, one floor of a multi-story building may have duct detectors wired together on a line that connects back to the control panel. Also, each duct detector on a line may be individually addressed from the control panel. Addressing individual devices allows a single duct detector to indicate an alarm condition at a specific location on a line, provides selective operation of specific duct detectors, and can also be useful for fault diagnosis and/or individual duct detector testing.

To perform fault diagnosis and/or individual duct detector testing, a self test mode may be used to eliminate the need to perform a smoke test. Smoke tests are undesirable because actual smoke is introduced into the duct and forced by the sensor. Rather than triggering an alarm indicating device by obstructing the light between the sensor and emitter or sensor/emitter device and reflector with smoke, the emitter's light output may be decreased or obstructed by other means to trigger an alarm indicating device.

One exemplary way to implement a self test mode to test a sensor may be to decrease the light that is emitted by the emitter or reflected by the reflector. Reducing the amount of light received by the sensor simulates the light reduction caused by smoke. Reducing the light received by the sensor may be caused by decreasing the light output of the emitter's LED or by decreasing the reflection characteristics of the reflector. Once, the light output is decreased the sensor may measure the reduction in light and trigger an alarm indicating device as discussed above.

Another exemplary embodiment used to test a sensor may be to implement a lens or filter to decrease the light that is detected by the sensor. The lens or filter may be placed within the light path between the emitter/sensor. By placing the lens or filter within the light path, the light received by the sensor is reduced thereby simulating the obstruction of light caused by smoke. Additionally, the lens or filter may be electro-mechanically inserted into the light path by any means known in the art, such as a relatively small motor. Generally, self test mode devices such as, the lens, filter, and LED for the light reduction or output of the emitter, may all be controlled remotely from a control panel as described above.

Figure 4:
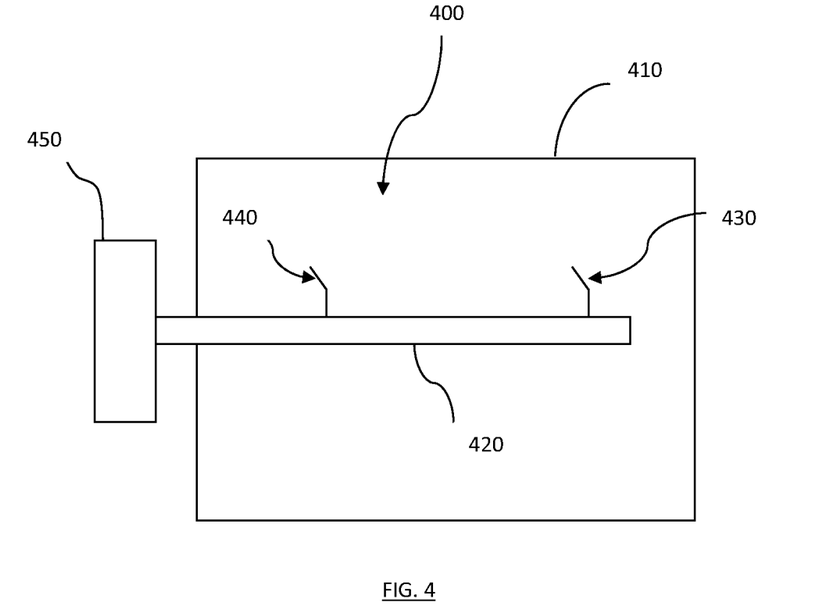
FIG. 4 is a side view depiction of a duct detector in accordance with the present disclosure.

FIG. 4 shows a cross-sectional view of a duct detector 400 consistent with one embodiment of the present invention. Those of ordinary skill in the art will recognize that the depicted system is highly-simplified for ease of explanation. The duct detector 400 is inserted and attached to an air duct 410. The duct detector 400 includes a rod 420 and a sensor 430 which is attached to a distal end of the rod as illustrated in FIG. 4. Opposite the sensor 430, an emitter 440 may be attached to the rod 420. Conversely, the position of the emitter 440 may be interchanged with the position of the sensor 430.

To insert the duct detector 400 into the air duct 410, a single penetration hole may be made in the wall of duct 410. The size of the penetration hole may be dependent on the size of the sensor 430, the emitter 440, and the rod 420. With this embodiment, it is the sensor 430 and emitter device 440 that are used to detect particles (i.e., smoke) within the duct. For example, the sensor 430 and emitter 440 may use technology that is similar to a beam detector for detecting particles (i.e., smoke) in air. However, the spacing between the sensor 430 and the emitter 440 may be used at much closer distances as compared to a beam detector. More specifically, it is the difference between the amount of light produced by the emitter 440 and the amount of light that is received by the sensor 430, as well as the distance between the two that is used to calculate the percent obscuration of the light. This percent of obscuration may be used to determine the presence of particles (i.e., smoke) between the emitter 440 and the sensor 430. Thus, as described above with reference to duct detector 300, when the percentage of obscuration passes a predetermined threshold, an alarm is triggered by duct detector 400. Again, to trigger an alarm or implement a self test mode, duct detector 400 may be in communication with alarm indicating devices or central control panels through wired or wireless connections 450. Additionally, to trigger an alarm, duct detector 400 may be also be equipped with self test mode devices, as described above with reference to FIG. 3. This eliminates the need for a smoke test when testing the sensor of duct detector 400.

Figure 5:
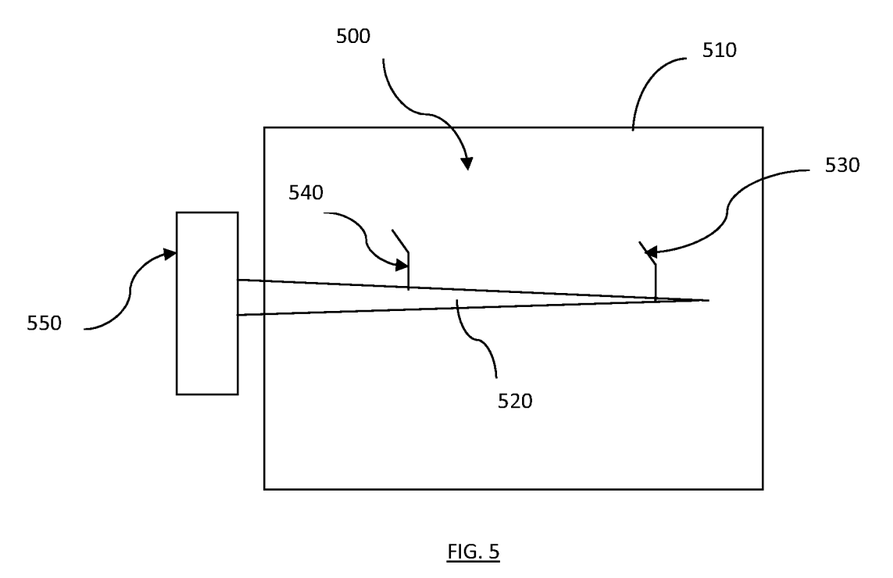
FIG. 5 is a side view depiction of a duct detector including a telescoping rod in accordance with the present disclosure.

FIG. 5 shows a cross-sectional view of a duct detector 500 consistent with one embodiment of the present invention. Those of ordinary skill in the art will recognize that the depicted system is highly-simplified for ease of explanation. The duct detector 500 is inserted and attached to an air duct 510. However, as depicted in FIG. 5, rods 320 and 420 of FIGS. 3 and 4, respectively, are substituted by a telescoping rod 520. The use of a telescoping rod 520 may be used to more easily adjust how far rod 520 penetrates the chamber of the duct 510. Here again, duct detector 500 may implement a sensor and emitter device 540 along with a reflector 530 as described with relation to FIG. 3. Duct detector 500 may also implement a sensor and emitter configuration as described with relation to FIG. 4. With either configuration a single penetration hole may be made in the duct 510 prior to inserting duct detector 500 into air duct 510. The size of the penetration hole may be dependent on the size of the duct detector 500. The telescoping rod 520 may then be substantially attached, for example, to the wall of the duct 510 by any means known in the art.

As described above with reference to duct detector 300, when the percentage of obscuration passes a predetermined threshold, an alarm indicating such may be triggered by duct detector 500. Again, to trigger an alarm or implement a self test mode, duct detector 500 may be in communication with alarm indicating devices or central control panels through wired or wireless connections 550. Additionally, to trigger an alarm, duct detector 500 may also be equipped with self test mode devices, as described above with reference to FIG. 3. This eliminates the need for a smoke test when testing the sensor of duct detector 500.

Figure 6:
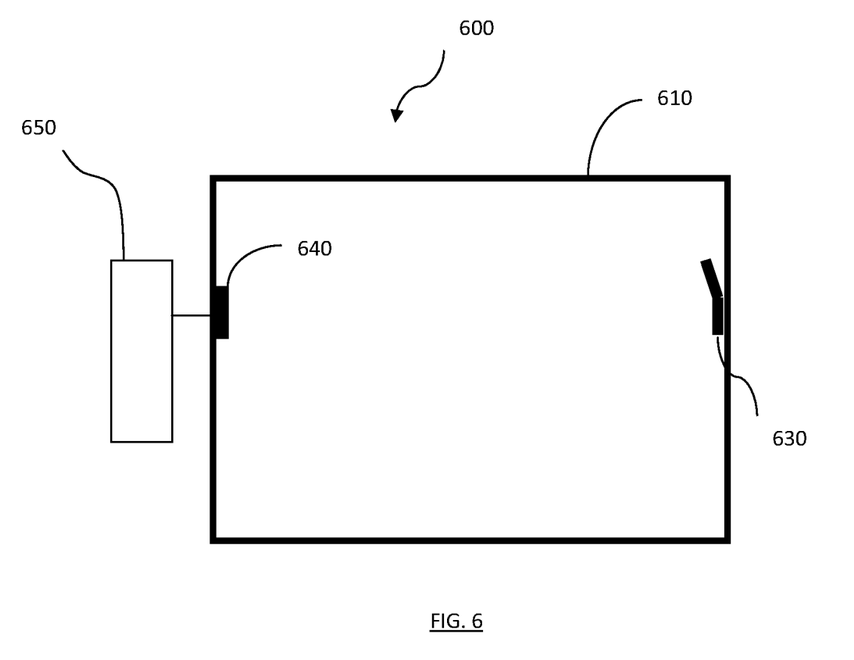
FIG. 6 is a side view depiction of a duct detector without a rod in accordance with the present disclosure.

FIG. 6 illustrates a cross-sectional view of a duct detector consistent with one embodiment of the present invention. Those of ordinary skill in the art will recognize that the depicted system is highly-simplified for ease of explanation. The duct detector 600 is substantially inserted and attached to opposing walls of air duct 610. However, as depicted in FIG. 6, rods 320 and 420 of FIGS. 3 and 4, respectively, are removed. Here again, duct detector 600 may implement a sensor and emitter device 640 along with a reflector 630 as described with relation to FIG. 3. However, sensor and emitter device 640 is attached to a wall of the duct 610 substantially opposite reflector 630. Duct detector 600 may also attach a sensor to the wall of the duct 610 substantially opposite an emitter. Any means known in the art may be used to attach the sensor and emitter device 640, reflector 630, emitter, or sensor to the wall of the duct and may be dependent on the size of the sensor and emitter device 640, reflector 630, emitter, or sensor used for the duct detector 600.

As described above with reference to duct detector 300, when the percentage of obstruction passes a predetermined threshold an alarm indicating such may be triggered by duct detector 600. Again, to trigger an alarm or implement a self test mode, duct detector 600 may be in communication with alarm indicating devices or central control panels through wired or wireless connections 650. Additionally, to trigger an alarm, duct detector 600 may be also be equipped with self test mode devices, as described above with reference to FIG. 3. This eliminating the need for a smoke test when testing the sensor of duct detector 600.

Figure 7A:
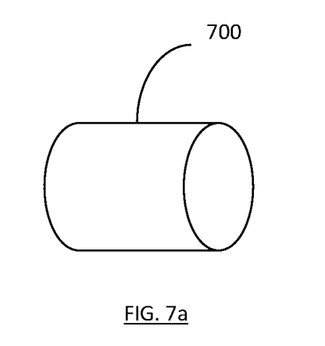
FIG. 7a is a side view depiction of a cover in accordance with the present disclosure.
Figure 7B:
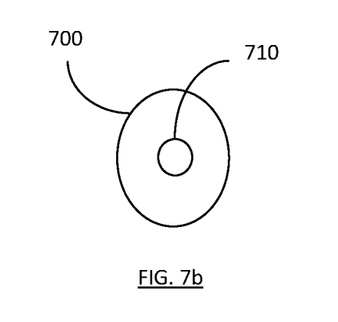
FIG. 7b is a front view depiction of a cover in accordance with the present disclosure.

FIGS. 7a and 7b illustrate one exemplary embodiment of a cover 700. FIG. 7a depicts a side view of the cover 700 and FIG. 7b depicts a front view of cover 700. The cover 700 may be coupled to a rod, telescoping rod, duct wall, sensor/emitter device, sensor, emitter, or reflector. The cover may be used to substantially prevent particles (i.e., dust) from accumulating on a sensor and emitter device, reflector, sensor, and emitter. Whatever shape used, the cover 700 substantially prevents dust accumulation while still allowing the emitter, sensor, and reflector to emit, sense, and reflect light 710, respectively. By covering the above mentioned structures, particles such as dust may be substantially prevented from overwhelming the structures. This may in turn prolong the accuracy of the duct detector in detecting particles (i.e., smoke) within a duct. By substantially preventing particles from overwhelming the sensor, emitter, and reflector structures the duct detector may substantially maintain its accuracy for detecting smoke for longer periods of time.

Figure 8:
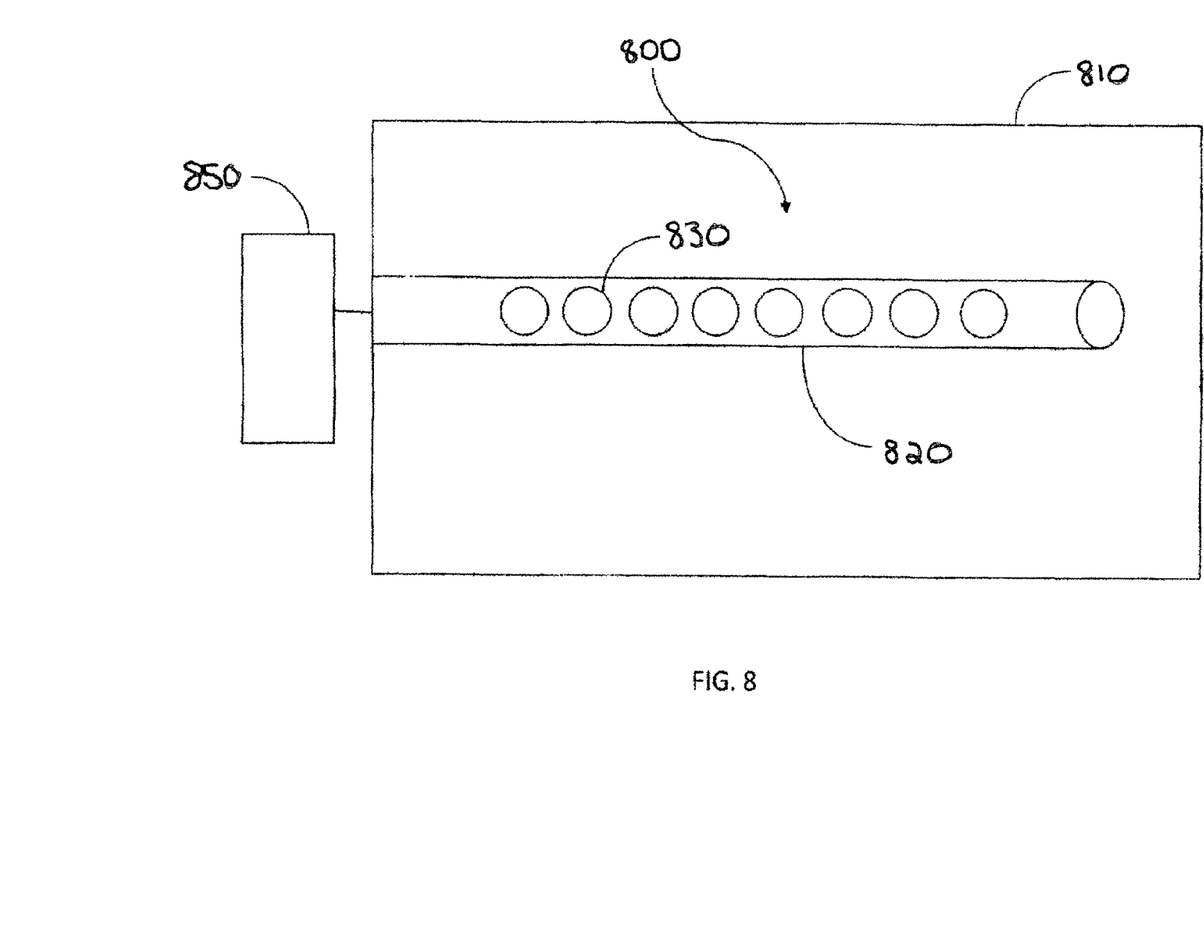
FIG. 8 is a side view depiction of a duct detector within a tubular rod in accordance with the present disclosure.

FIG. 8 shows a side view of a duct detector 800 consistent with one embodiment of the present invention. Those of ordinary skill in the art will recognize that the depicted system is highly-simplified for ease of explanation. The duct detector 800 is substantially inserted and attached to an air duct 810. However, as depicted in FIG. 8, rods 320 and 420 of FIGS. 3 and 4, respectively, are substituted by a substantially tubular rod 820. The use of a tubular rod 820 may be used to protect the sensor and emitter device, sensor, emitter, or reflector while allowing smoke or other particles to travel through ventilation structures 830. By implementing a sensor and emitter device within the tubular rod 820, and on one side of the ventilation structures 830, and a reflector within the tubular rod 820, and on the other side of the ventilation structure 830, the particles (i.e., smoke) may pass through the tubular rod 820 and in between the sensor and emitter device and reflector. Likewise, the duct detector 800 may also implement a sensor and emitter within the tubular rod 820. The sensor located within the tubular rod 820 across from the emitter which may also be located substantially within the tubular rod 820. Between the sensor and emitter, ventilation structures 830 may be used to allow particles (i.e., smoke) to pass through the tubular rod 820 and enter the line of site between the emitter and sensor. With either configuration a single penetration hole may be made in the duct 810 prior to inserting duct detector 800 into air duct 810. The size of the penetration hole may be dependent on the size of the duct detector 800. The tubular rod 820 may then be substantially attached, for example, to the wall of the duct 810 by any means known in the art.

As described above with reference to duct detector 300, when the percentage of obstruction passes a predetermined threshold, an alarm indicating such may be triggered by duct detector 800. Again, to trigger an alarm or implement a self test mode, duct detector 800 may be in communication with alarm indicating devices or central control panels through wired or wireless connections 850. Additionally, to trigger an alarm, duct detector 800 may be also be equipped with self test mode devices, as described above with reference to FIG. 3. This eliminates the need for a smoke test when testing the sensor of duct detector 800.

The improved duct detector disclosed herein advantageously reduces the number of holes required to install a duct detector within a duct system. In fact, only one installation hole may be created within the duct per at least one duct detector that is to be installed within a duct.

The improved duct detector disclosed herein advantageously uses the duct itself as a chamber for detecting particles (i.e., smoke) which obviates the need to use airflow and differential pressure devices. Thus, there is no longer a need to confirm the presence of airflow before testing the operability of the duct detectors. Likewise, upstream and downstream orientation concerns regarding exhaust tubes and sampling tubes are eliminated by implementing the improved duct detector. Furthermore, the improved duct detector allows for self testing with a self test mode. Consequently, the improved duct detector reduces the labor costs and hazards associated with manufacturing, installing, and testing duct detectors.

While the present invention has been disclosed with reference to certain embodiments, numerous modifications, alterations and changes to the described embodiments are possible without departing from the sphere and scope of the present disclosure, as defined in the appended claims. Accordingly, it is intended that the present invention not be limited to the described embodiments, but that it has the full scope defined by the language of the following claims, and equivalents thereof.

What is claimed is:

1. A particle detection unit comprising:
  a duct detector, for disposal within a duct, including a rod having a first and a second end, the first end distal the second end, a reflector attached to the rod adjacent the first end, a sensor/emitter device attached to the rod and spaced apart from the reflector at a second end,
  wherein the sensor/emitter device is configured to detect particles disposed between the first and second ends;
  wherein the duct detector is operatively connected to a central control panel located remote from the duct detector, the central control panel configured to initiate a remote self-test of the duct detector; and
  wherein the self-test of the duct detector comprises decreasing the sensor/emitter's light output by a predetermined amount to simulate the light reduction caused by a predetermined amount of smoke.

2. The particle detection unit of claim 1, wherein the duct detector is disposed in a detection chamber defined by the duct from a duct system.

3. The particle detection unit of claim 1, wherein the sensor/emitter device is operably coupled to a control panel located outside the duct.

4. The particle detection unit of claim 1, wherein the sensor/emitter device is operably coupled to an alarm indicating device.

5. The particle detection unit of claim 1, wherein the sensor/emitter device is operably coupled to a control panel through a pair of bidirectional communication lines.

6. The particle detection unit of claim 1, further comprising at least one cover coupled to at least one of the sensor, the emitter and the reflector for preventing particles from accumulating on the at least one of the sensor, the emitter and the reflector.

7. A particle detection unit comprising:
  a duct detector, disposed within a duct and defined by a rod having a first and a second end, the first end distal the second end;
  an emitter attached to the rod adjacent the first end; and
  a sensor attached to the rod and spaced apart from the reflector;
  wherein the duct detector is operatively connected to a central control panel located remote from the duct detector, the central control panel configured to initiate a remote self-test of the duct detector; and
  wherein the remote self-test of the duct detector comprises decreasing the emitter's light output level by a predetermined amount to simulate the light reduction caused by a predetermined amount of smoke.

8. The particle detection unit of claim 7, further comprising at least one cover coupled to at least one of the sensor, the emitter and the reflector for preventing particles from accumulating on the at least one of the sensor, the emitter and the reflector.

9. A method, comprising:
  installing a duct detector within a duct defined by a wall having an inner surface; the duct detector comprising a rod having a first end and a second end, the first end distal to the second end, a reflector attached to the rod adjacent the first end, and a sensor and emitter device attached to the rod and spaced apart from the reflector;

attaching the duct detector to the inner surface;

initiating a self-test of a duct detector from a remote location via a central control panel, the self-test comprising decreasing the sensor and emitter device's light output by a predetermined amount to simulate the light reduction caused by a predetermined amount of smoke.

10. The method of claim 9 further comprising, creating a single hole through the wall of the duct for inserting the duct detector into the duct.

11. The method of claim 9 further comprising, coupling the sensor and emitter device to an alarm indicating device.

12. The method of claim 9 further comprising, coupling the sensor and emitter device to a control panel located outside the duct.

13. The method of claim 9 further comprising, coupling the sensor and emitter device to a control panel through a pair of bidirectional communication lines.

14. The method of claim 9, wherein the duct detector is disposed in a detection chamber comprising the duct from a duct system.

* * * * *